United States Patent
Laubacher et al.

(10) Patent No.: US 7,265,550 B2
(45) Date of Patent: Sep. 4, 2007

(54) USE OF TWO OR MORE SENSORS IN A NUCLEAR QUADRUPOLE RESONANCE DETECTION SYSTEM TO IMPROVE SIGNAL-TO-NOISE RATIO

(75) Inventors: Daniel B. Laubacher, Wilmington, DE (US); James D. McCambridge, Swarthmore, PA (US); Charles Wilker, Wilmington, DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 6 days.

(21) Appl. No.: 11/051,863

(22) Filed: Feb. 4, 2005

(65) Prior Publication Data

US 2007/0176600 A1    Aug. 2, 2007

Related U.S. Application Data

(60) Provisional application No. 60/557,235, filed on Mar. 29, 2004, provisional application No. 60/541,660, filed on Feb. 4, 2004.

(51) Int. Cl.
   *G01V 3/00* (2006.01)
(52) U.S. Cl. ...................................... 324/318
(58) Field of Classification Search ................ 324/318
   See application file for complete search history.

(56) References Cited

U.S. PATENT DOCUMENTS

| | | | |
|---|---|---|---|
| 3,373,348 A | 3/1968 | Vanier et al. | |
| 3,764,892 A | 10/1973 | Rollwitz | |
| 4,027,768 A | 6/1977 | Riessen | |
| 4,072,768 A | 2/1978 | Fraser et al. | |
| 4,514,691 A | 4/1985 | De Los Santos et al. | |
| 5,036,279 A | 7/1991 | Jonsen | |
| 5,135,908 A | 8/1992 | Yang et al. | |
| 5,206,592 A | 4/1993 | Buess et al. | |
| 5,233,300 A | 8/1993 | Buess et al. | |
| 5,258,710 A | 11/1993 | Black et al. | |
| 5,262,394 A | 11/1993 | Wu et al. | |
| 5,276,398 A | 1/1994 | Withers et al. | |
| 5,351,007 A | 9/1994 | Withers et al. | |
| 5,418,213 A | 5/1995 | Tanaka et al. | |
| 5,457,385 A | 10/1995 | Sydney et al. | |
| 5,583,437 A | 12/1996 | Smith et al. | |
| 5,585,723 A | 12/1996 | Withers | |
| 5,592,083 A | 1/1997 | Magnuson et al. | |
| 5,594,338 A | 1/1997 | Magnuson | |

(Continued)

FOREIGN PATENT DOCUMENTS

EP    0 426 851    5/1991

(Continued)

OTHER PUBLICATIONS

He, D.F. et al., "Metal detector based on high-Tc RF SQUID", Physica C 378-381 (2002) pp. 1404-1407.

(Continued)

*Primary Examiner*—Brij Shrivastav
*Assistant Examiner*—Megann E Vaughn

(57) ABSTRACT

The use of two or more sensors tuned to the same nuclear quadrupole resonance frequency and detecting the nuclear quadrupole resonance signal results in improved signal-to-noise ratio and therefore improved nuclear quadrupole resonance detection system performance.

12 Claims, 2 Drawing Sheets

U.S. PATENT DOCUMENTS

| | | |
|---|---|---|
| 5,656,937 A | 8/1997 | Cantor |
| 5,661,400 A | 8/1997 | Plies et al. |
| 5,750,473 A | 5/1998 | Shen |
| 5,751,146 A | 5/1998 | Hrovat |
| 5,804,967 A | 9/1998 | Miller et al. |
| 5,814,987 A | 9/1998 | Smith et al. |
| 5,814,989 A | 9/1998 | Smith et al. |
| 5,814,992 A | 9/1998 | Busse-Gravitz et al. |
| 5,872,080 A | 2/1999 | Arendt et al. |
| 5,952,269 A | 9/1999 | Ma et al. |
| 5,973,495 A | 10/1999 | Mansfield |
| 5,986,455 A | 11/1999 | Magnuson |
| 5,999,000 A | 12/1999 | Srinivasan |
| 6,026,719 A | 2/2000 | Anderson |
| 6,054,856 A | 4/2000 | Garroway et al. |
| 6,088,423 A | 7/2000 | Krug et al. |
| 6,091,240 A | 7/2000 | Smith et al. |
| 6,104,190 A | 8/2000 | Buess et al. |
| 6,108,569 A | 8/2000 | Shen |
| 6,150,816 A | 11/2000 | Srinivasan |
| 6,166,541 A | 12/2000 | Smith et al. |
| 6,169,399 B1 | 1/2001 | Zhang et al. |
| 6,194,898 B1 | 2/2001 | Magnuson et al. |
| 6,201,392 B1 | 3/2001 | Anderson et al. |
| 6,218,943 B1 | 4/2001 | Ellenbogen |
| 6,242,918 B1 | 6/2001 | Miller et al. |
| 6,291,994 B1 | 9/2001 | Kim et al. |
| 6,335,622 B1 | 1/2002 | James et al. |
| 6,370,404 B1 | 4/2002 | Shen |
| D459,245 S | 6/2002 | Power |
| 6,420,872 B1 | 7/2002 | Garroway et al. |
| 6,486,838 B1 | 11/2002 | Smith et al. |
| 6,538,445 B2 | 3/2003 | James et al. |
| 6,541,966 B1 | 4/2003 | Keene |
| 6,556,013 B2 | 4/2003 | Withers |
| 6,566,873 B1 | 5/2003 | Smith et al. |
| 6,590,394 B2 | 7/2003 | Wong et al. |
| 6,617,591 B1 | 9/2003 | Simonson et al. |
| 6,653,917 B2 | 11/2003 | Kang et al. |
| 6,751,489 B2 | 6/2004 | Shen |
| 6,751,847 B1 | 6/2004 | Brey et al. |
| 6,777,937 B1 | 8/2004 | Miller et al. |
| 6,819,109 B2 | 11/2004 | Sowers et al. |
| 6,822,444 B2 | 11/2004 | Lai |
| 6,847,208 B1 | 1/2005 | Crowley et al. |
| 6,952,163 B2 | 10/2005 | Muey et al. |
| 6,956,476 B2 | 10/2005 | Buess et al. |
| 6,958,608 B2 | 10/2005 | Takagi et al. |
| 7,049,814 B2 | 5/2006 | Mann |
| 7,106,058 B2 | 9/2006 | Wilker et al. |
| 2002/0068682 A1 | 6/2002 | Shen |
| 2002/0153891 A1 | 10/2002 | Smith et al. |
| 2002/0156362 A1 | 10/2002 | Bock et al. |
| 2002/0169374 A1 | 11/2002 | Jevtic |
| 2002/0190715 A1 | 12/2002 | Marek |
| 2003/0020553 A1 | 1/2003 | Gao et al. |
| 2003/0062896 A1 | 4/2003 | Wong et al. |
| 2003/0071619 A1 | 4/2003 | Sauer et al. |
| 2003/0119677 A1 | 6/2003 | Qiyan et al. |
| 2003/0136920 A1 | 7/2003 | Flores et al. |
| 2004/0124840 A1 | 7/2004 | Reykowski |
| 2004/0222790 A1 | 11/2004 | Karmi et al. |
| 2004/0251902 A1 | 12/2004 | Takagi et al. |
| 2005/0104593 A1 | 5/2005 | Laubacher et al. |
| 2005/0122109 A1 | 6/2005 | Wilker et al. |
| 2005/0140371 A1 | 6/2005 | Alvarez et al. |
| 2005/0146331 A1 | 7/2005 | Flexman et al. |
| 2005/0206382 A1 | 9/2005 | Laubacher et al. |
| 2005/0248345 A1 | 11/2005 | Alvarez |
| 2005/0258831 A1 | 11/2005 | Alvarez |
| 2005/0264289 A1 | 12/2005 | Alvarez |
| 2005/0270028 A1 | 12/2005 | Alvarez et al. |
| 2006/0012371 A1 | 1/2006 | Laubacher et al. |
| 2006/0038563 A1 | 2/2006 | Cisholm et al. |
| 2006/0082368 A1 | 4/2006 | McCambridge |
| 2006/0119360 A1 | 6/2006 | Yamamoto et al. |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269 108 | 10/1993 |
| JP | 07 265 278 | 10/1995 |
| WO | WO92/17793 | 10/1992 |
| WO | WO92/17794 | 10/1992 |
| WO | WO92/19978 | 11/1992 |
| WO | WO92/21989 | 12/1992 |
| WO | WO94/05022 | 3/1994 |
| WO | WO95/34096 | 12/1995 |
| WO | WO 96/39636 | 12/1996 |
| WO | WO96/39636 | 12/1996 |
| WO | WO96/39638 | 12/1996 |
| WO | WO98/37438 | 8/1998 |
| WO | WO98/54590 | 12/1998 |
| WO | WO99/45409 | 9/1999 |
| WO | WO99/50689 | 10/1999 |
| WO | WO 00/70356 | 11/2000 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 2004/001454 A | 6/2004 |
| WO | WO 2004/102596 | 11/2004 |
| WO | WO 05/059582 A1 | 6/2005 |

OTHER PUBLICATIONS

Miller, et al., "Performance of a High-Termperature Superconducting Probe for In Vivo Microscopy at 2.0 T", Magnetic Resonance in Medicine, (1999) pp. 72-79, vol. 41.

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada (Sep. 14-17, 1993) Sep. 14, 1993 XP 010118071.

W. A. Edelstein et al., A Signal-to-noise calibration procedure for NMR imaging systems, Medical Physics, vol. 11 (2) Mar./Apr. 1984, pp. 180-185.

T. Hirschfeld, "Short Range Remote Nqr Measurements", Journal of Molecular Structure, (1980) pp. 63-77, vol. 58, Elsevier Scientific Publishing Company, Amsterdam.

Garroway, et al., "Remote Sensing by Nuclear Quadrupole Resonance", IEEE Transactions on Geoscience and Remote Sensing, Jun. 2001, pp. 1108-1118, vol. 39, No. 6.

Garroway, et al., "Narcotics and explosives detection by N pure NQR", SPIE, (1993) pp. 318-327, vol. 2092.

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

Bendall, et. al., "Elimination of Coupling between Cylindrical Transmit Coils and Surface-Receive Coils for in Vivo NMR" Magnetic Resonance in Medicine v3 p. 157-163, 1986.

Black, et al., "A High-Temperature Superconducting Receiver For Nuclear Magnetic Resonance Microscopy", Science, vol. 259, pp. 793-795 Feb. 5, 1993.

Black, et al., "Performance Of A High-Temperature Superconducting Resonator For High-Field Imaging", Journal Of Magnetic Resonance, pp. 74-80 (1995).

Colton, et. al., "Making the World a Safer Place", Science, v. 299, i.5611, pp. 1324-1325, Feb. 2006.

Fisher, et al., "A Versatile Computer-Controlled Pulsed Nuclear Quadrupole Resonance Spectrometer", Review of Scientific Instruments, v70, No. 12, p. 4678, Dec. 1999.

Hill, "Improved Sensitivity of NMR Spectroscopy Probes By Use Of High-Temperature Superconductive Detection Coils", IEEE Transactions On Applied Superconductivity, vol. 7, pp. 3750-3753, Jun. 1997.

Roemer, et. al., "The NMR Phased Array", Magnetic Resonance In Medicine 16, pp. 192-225, 1990.

Withers, et al., "Thin-Film HTD Probe Coils For Magnetic-Resonance Imaging", IEEE Transactions On Applied Superconductivity, vol. 3, pp. 2450-2453, Mar. 1993.

Landers, et al., "Electronic Effects and Molecular Motion in β-Octahydro-1,3,5,7-tetranitro-1,3,5,7-tetrazocine Bases on $^{14}$N Nuclear Quadrupole Resonance Spectroscopy", American Chemical Society, J. Phys. Chem., 85, pp. 2618-2623, 1981.

Karpowicz, et. Al., "Librational Motion of Hexahydro-1,3,5-trinitro-s-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87, pp. 2109-2112, 1983.

Volpicelli, et. al., "Locked rf Spectrometer for Nuclear Quadrupole Resonance", The Review of Scientific Instruments, v.25, No. 2, pp. 150-153, Feb. 1965.

Benedek, et. al., "Precise Nuclear Resonance Thermometer", The Review of Scientific Instruments, v.28, No. 2, pp. 92-95, Feb. 1957.

Ernst, "Magnetic Resonance with Stochastic Excitation", Journal of Magnetic Resonance 3, pp. 10-27, 1970.

Klainer, et. al., "Fourier Transform Nuclear Quadrupole Resonance Spectroscopy", Fourier, Hadamard, and Hilbert Transforms in Chemistry, pp. 147-182, 1982.

USE OF TWO OR MORE SENSORS IN A NUCLEAR QUADRUPOLE RESONANCE DETECTION SYSTEM TO IMPROVE SIGNAL-TO-NOISE RATIO

This application claims the benefit of U.S. Provisional Application No. 60/541,660, filed on Feb. 4, 2004, and U.S. Provisional Application No. 60/557,235, filed on Mar. 29, 2004, each of which is incorporated in its entirety as a part hereof for all purposes.

FIELD OF THE INVENTION

This invention relates to a nuclear quadrupole resonance detection system and to the use of two or more sensors tuned to the same nuclear quadrupole resonance frequency when detecting the nuclear quadrupole resonance signal, thereby providing improved nuclear quadrupole resonance detection system performance.

BACKGROUND OF THE INVENTION

The use of nuclear quadrupole resonance (NQR) as a means of detecting explosives and other contraband has been recognized for some time. See e.g. T. Hirshfield et al, *J. Molec. Struct.* 58, 63 (1980); A. N. Garroway et al, *Proc. SPIE* 2092, 318 (1993); and A. N. Garroway et al, *IEEE Trans. on Geoscience and Remote Sensing* 39, 1108 (2001).

NQR provides some distinct advantages over other detection methods. NQR requires no external magnet such as required by nuclear magnetic resonance. NQR is sensitive to the compounds of interest, i.e. there is a specificity of the NQR frequencies.

One technique for measuring NQR in a sample is to place the sample within a solenoid coil that surrounds the sample. The coil provides a radio frequency (RF) magnetic field that excites the quadrupole nuclei in the sample and results in their producing their characteristic resonance signals. This is the typical apparatus configuration that might be used for scanning mail, baggage or luggage.

There is also need for a NQR detector that permits detection of NQR signals from a source outside the detector, e.g. a wand detector, that could be passed over persons or containers as is done with existing metal detectors. Problems associated with such detectors using conventional systems are the decrease in detectability with distance from the detector coil and the associated equipment needed to operate the system.

A detection system can have one or more devices (such as coils) that both transmit and receive, or it can have separate devices (such as coils) that only transmit and only receive. A transmit, or transmit and receive, coil of an NQR detection system provides a magnetic field that excites the quadrupole nuclei in the sample and results in their producing their characteristic resonance signals that the coil receives. As the NQR signals have low intensity and short duration, the transmit, receive, or transmit and receive, coil preferably has a high quality factor (Q). The transmit, receive, or transmit and receive, coil has typically been a copper coil and therefore has a of about $10^2$.

It can be advantageous to use a transmit, receive, or transmit and receive coil, made of a high temperature superconductor (HTS) rather than copper since the HTS self-resonant coil has a Q of the order of $10^3$-$10^6$. The large Q of the HTS self-resonant coil produces large magnetic field strengths during the RF transmit pulse and does so at lower RF power levels. This dramatically reduces the amount of transmitted power required to produce NQR signals for detection, and thereby reduces the size of the RF power supply sufficiently so that it can be run on portable batteries.

The large Q of the HTS self-resonant coil also plays an important role during the receive time. In view of the low intensity NQR signal, it is important to have a signal-to-noise ratio (S/N) as large as possible. The signal-to-noise ratio is proportional to the square root of Q so that the use of the HTS self-resonant coil results in an increase in S/N by a factor of 10-100 over that of the copper system.

These advantages during both the transmit and the receive times enable a detector configuration that is small and portable. In particular, the use of a high temperature superconductor sensor receive coil prepared from a high temperature superconductor material, provides a distinct advantage over the use of an ordinary conductor coil.

An object of the present invention is to provide a NQR detection system with improved performance, particularly where the transmit, receive, or transmit and receive coil, is made of a high temperature superconductor.

SUMMARY OF THE INVENTION

One embodiment of this invention is a method of detecting nuclear quadrupole resonance in an object by
  a) providing two or more sensors tuned to a specified nuclear quadrupole resonance frequency, wherein each sensor receives the specified nuclear quadrupole resonance signal;
  b) applying a radio frequency magnetic field to the object; and
  c) adding coherently the signals detected by the sensors.

Another embodiment of this invention is a nuclear quadrupole resonance detection system for detecting nuclear quadrupole resonance in an object, comprising:
  a) two or more sensors tuned to a specified nuclear quadrupole resonance frequency, wherein each sensor receives the specified nuclear quadrupole resonance signal; and
  b) means to add coherently nuclear quadrupole resonance signals detected by the sensors.

A further embodiment of this invention is a nuclear quadrupole resonance detection system for detecting nuclear quadrupole resonance in an object, comprising:
  a) two or more sensors tuned to a specified nuclear quadrupole resonance frequency, wherein each sensor receives the specified nuclear quadrupole resonance signal; and
  b) an electrical path from each sensor to a combination point at which the signals are added, wherein the signals received across the paths add constructively at the combination point.

Preferably, the two or more sensors are used solely for sensing, i.e. receiving, the NQR signal, and one or more separate coils are used as the transmit, i.e. excitation, coils to provide the RF magnetic field that excites the quadrupole nuclei in the object to be scanned. Preferably, the two or more sensors are high temperature superconductor coils. More preferably, the two or more sensors are each comprised of a high temperature superconductor self-resonant planar coil, or of two or more coupled high temperature superconductor self-resonant planar coils.

This invention for improving the signal-to-noise ratio and thereby the performance of a nuclear quadrupole resonance detection system is especially important when the nuclear quadrupole resonance detection system is used for detecting the nuclear quadrupole resonance of explosives, drugs and other contraband.

DETAILED DESCRIPTION OF THE PREFERRED EMBODIMENTS

Figure 1:
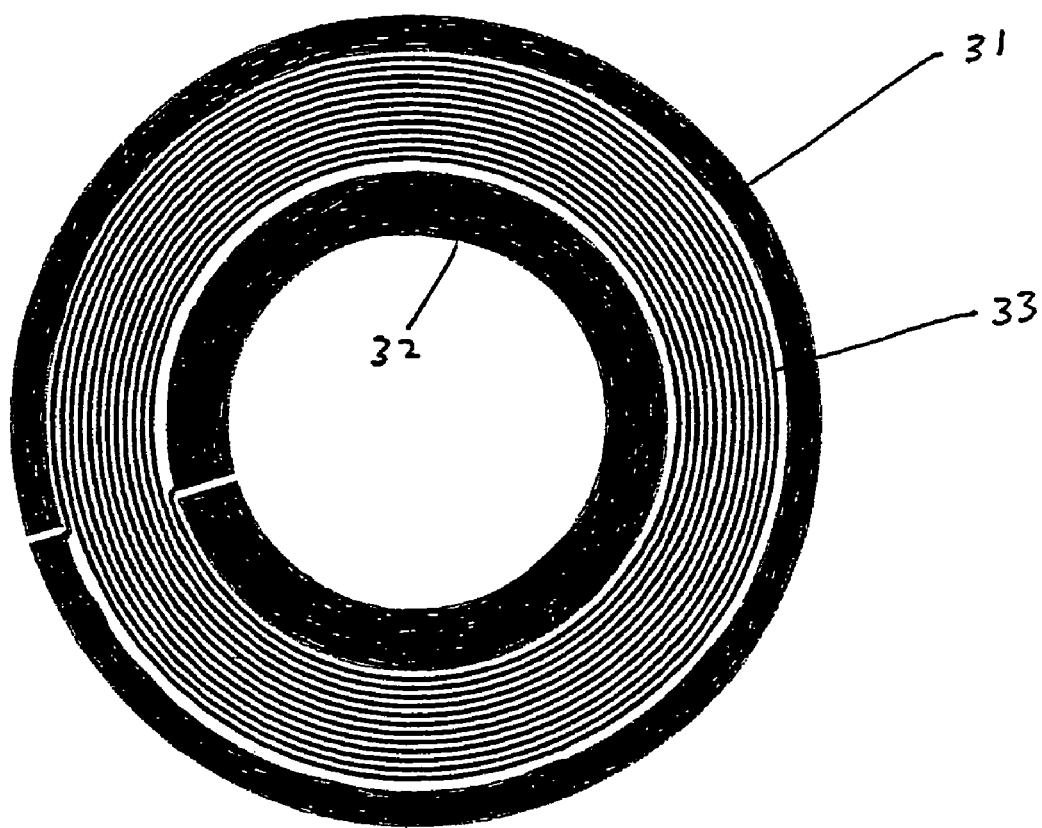
FIG. 1 shows the HTS coil design of an HTS coil used in the example.

This invention provides a method for increasing the signal-to-noise ratio of a NQR detection system for scanning a potential source of NQR, and also provides a NQR detection system that provides this increased performance. To accomplish this, two or more sensors are tuned to a specified nuclear quadrupole resonance frequency, and the signals detected by each sensor are added coherently. Two or more sensors are tuned to a "specified" nuclear quadrupole resonance frequency in the manner contemplated by this invention when each sensor is tuned to a frequency within a given nuclear quadrupole resonance emission line so that even if each sensor is not tuned to exactly the same frequency, they are all still detecting the same emission line.

A "sensor" as used in this invention is a receive device, such as a receive coil, and the two or more sensors used to detect nuclear quadrupole resonance in a sample or object will typically be used as receive coils only. In certain embodiments, it may be possible to use them as transmit and receive coils, but, preferably, separate coils are used to transmit the RF signal, and the sensors (as their name implies) are used solely as receive coils.

The transmit coils used in this invention can be made of copper, silver, aluminum or a high temperature superconductor. A copper, silver or aluminum coil is preferably in the form of a shielded-loop resonator (SLR) coil. SLR's have been developed to eliminate the detuning effect of the electrical interaction between the coil and the surrounding material. Preferably, a copper SLR transmit coil is used to apply the RF signal to the sample or object to be scanned. In an NQR detection system, provision must of course be made for a power supply to supply power for transmitting the RF pulse.

Preferably, the two or more sensors are high temperature superconductor (HTS) coils. A high temperature superconductor coil is preferably in the form of a self-resonant planar coil, i.e. a surface coil, with a coil configuration of HTS on one or both sides of a substrate. High temperature superconductors are those that superconduct above 77K. High temperature superconductors used to form a HTS self-resonant coil are preferably selected from the group consisting of $YBa_2Cu_3O_7$, $Tl_2Ba_2CaCu_2O_8$, $TlBa_2Ca_2Cu_3O_9$, $(TlPb)Sr_2CaCu_2O_7$ and $(TlPb)Sr_2Ca_2Cu_3O_9$. Most preferably, the high temperature superconductor is $YBa_2Cu_3O_7$ or $Tl_2Ba_2CaCu_2O_8$. A HTS self-resonant coil can be formed by various known techniques. A preferred technique for forming a $Tl_2Ba_2CaCu_2O_8$ coil is described in the example.

It is often advantageous to be able to fine tune the resonance frequency of a sensor. One means for accomplishing such tuning is to use two or more coupled high temperature superconductor self-resonant coils. The resonance frequency of the fundamental symmetric mode of coupled high temperature superconductor self-resonant coils can be varied by mechanically displacing the coils with respect to one another, and such tunable coupled coils may be used as a HTS sensor. A coil used in a coupled configuration is preferably a planar, i.e. surface, coil. A planar coil may have a HTS coil configuration on only one side of the substrate, or may have essentially identical HTS coil configurations on both sides of the substrate. Most preferably, each sensor herein is comprised of a high temperature superconductor self-resonant planar coil, or two or more coupled high temperature superconductor self-resonant planar coils.

As indicated above, when two or more coupled high temperature superconductor self-resonant coils are used as a sensor, the resonance frequency of the fundamental symmetric mode of the coupled high temperature self-resonant coils can be varied by mechanically displacing the coils with respect to one another. Means for tuning the resonance frequency of a sensor to a specified nuclear quadrupole resonance frequency thus includes the mechanical displacement of coupled coils as described above.

Alternatively, for a sensor comprised of one or more high temperature superconductor self-resonant coil coils, means for tuning the resonance frequency of the sensor to a specified nuclear quadrupole resonance frequency may include a circuit. The circuit can be comprised of a single loop or coil to inductively couple the circuit to the high temperature superconductor self-resonant sensor, a reactance in series with the single loop or coil, and means for connecting and disconnecting the reactance to and from the single loop or coil. In essence, the tuning circuit is resonated, which causes a mode split by coupling to the self-resonant high temperature superconductor sensor.

In the tuning circuit, the single loop or coil can be made of a regular conductor such as copper or a high temperature superconductor. The reactance can be an inductance, capacitance or combination of both. Means for connecting and disconnecting the reactance to and from the single loop or coil may include at least one mechanical switch, or electrical switch such as a diode. Preferably, the reactance can be varied so that the resonance frequency can be adjusted to more than one frequency. One way of providing a variable reactance is to utilize as the reactance two or more capacitors in parallel, each of which can be individually connected to or disconnected from the single loop or coil. Alternatively, a variable reactance can be prepared from two or more inductors in series, each of which can be individually connected to or disconnected from the single loop or coil by a mechanical or electrical switch that can short-circuit the inductor and thereby essentially remove it from the circuit.

The NQR signals detected by the two or more sensors used in this invention can be added coherently, i.e. the phases of the individual signals are, by various analog and digital techniques, adjusted to add constructively. In the analog technique for coherent addition, the electrical path from each sensor to the combination point, at which the signals are added, is adjusted so that the signals add constructively at the combination point. When the sensors are essentially equidistant from the object that is the source of the nuclear quadrupole resonance signal, the electrical path from each sensor to the combination point can be made essentially identical, thereby insuring that the signals add constructively at the combination point.

Means for adding signals may also be provided, which may include a microprocessor for performing various digital techniques for coherent addition. In a digital technique, for example, the signal detected by each sensor may be multiplied before combination by a constant complex factor that can be measured or calculated to correct for phase differences between the signal paths and thereby insure that the signals add constructively at the combination point. The constant complex factor is specific to the electrical path from each sensor to the combination point. Typically, the signals will be amplified before they are added.

In this invention, the advantages in using in an NQR system an array of two or more sensors over the use of a single sensor can be seen as follows. The signal S obtained by using an array of n sensors and coherently adding the signals is proportional to n. Assuming that the noise present is random, the noise N, after the coherent addition, is proportional to $n^{0.5}$. Therefore S/N is proportional to $n^{0.5}$, i.e. is proportional to the square root of n. An array of two sensors therefore increases S/N by a factor of 1.4. An array of four sensors increases S/N by a factor of 2.

The use of HTS self-resonant coils as sensors makes the instant invention especially attractive. The HTS self-resonant coils have high Q's and relatively small size and make the use of an array of two or more sensors more feasible. If one or more HTS coils are used herein as sensors, provision must be made for cooling the HTS to at least liquid nitrogen temperature.

The advantageous effects of this invention are demonstrated by an example, as described below. The embodiments of the invention on which the example is based are illustrative only, and do not limit the scope of the appended claims. The purpose of the example is to demonstrate the increase in S/N when two sensors are used to detect a frequency and the signals from the sensors are added coherently.

HTS self-resonant sensors are provided, each of which is two coupled essentially identical $Tl_2Ba_2CaCu_2O_8$ planar coils. Each of the coupled coils is on a lanthanum aluminate ($LaAlO_3$) substrate with the coil design configuration shown in FIG. 1 on both sides of the substrate.

A clean, polished single crystal $LaAlO_3$ substrate with a diameter of 2 inches (5.1 cm) and an approximate thickness of 0.02 inches (0.5 mm) was obtained from Litton Airtron, Morris Plains, N.J. Off-axis magnetron sputtering of a Ba:Ca:Cu oxide target is used to deposit, at room temperature (about 20° C.), an amorphous precursor Ba:Ca:Cu oxide film on both sides of the substrate. This amorphous Ba:Ca:Cu oxide film is about 550 nm thick and had a stoichiometry of about 2:1:2. The precursor film is then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_8$ phase on both sides of the substrate.

The $Tl_2Ba_2CaCu_2O_8$ is then coated with photoresist on both sides and baked. A coil design mask with the design shown in FIG. 1 is prepared. The coil has an inner radius of about 10.5 mm and an outer radius of about 22.5 mm. The outermost HTS ring 31 of the coil is about 2 mm wide and the innermost HTS ring 32 is about 3.5 mm wide. The intermediate HTS rings 33 are about 250 μm wide with about 250 μm gaps between the rings. The coil design mask is then centered on the photoresist covering the $Tl_2Ba_2CaCu_2O_8$ film on the front side of the substrate and exposed to ultraviolet light. The coil design mask is then centered on the photoresist covering the $Tl_2Ba_2CaCu_2O_8$ film on the back side of the substrate and exposed to ultraviolet light. The resist is then developed on both sides of the substrate and the portion of the $Tl_2Ba_2CaCu_{28}$ film exposed when the resist is developed is etched away by argon beam etching. The remaining photoresist layer is then removed by an oxygen plasma.

The result is a coil structure comprised of the single crystal $LaAlO_3$ substrate with a high temperature superconductor $Tl_2Ba_2CaCu_2O_8$ pattern of the configuration shown in FIG. 1 centered on each side of the single crystal $LaAlO_3$ substrate. The process is repeated three times in essentially the same way to produce three coils essentially identical to the first.

Figure 2:
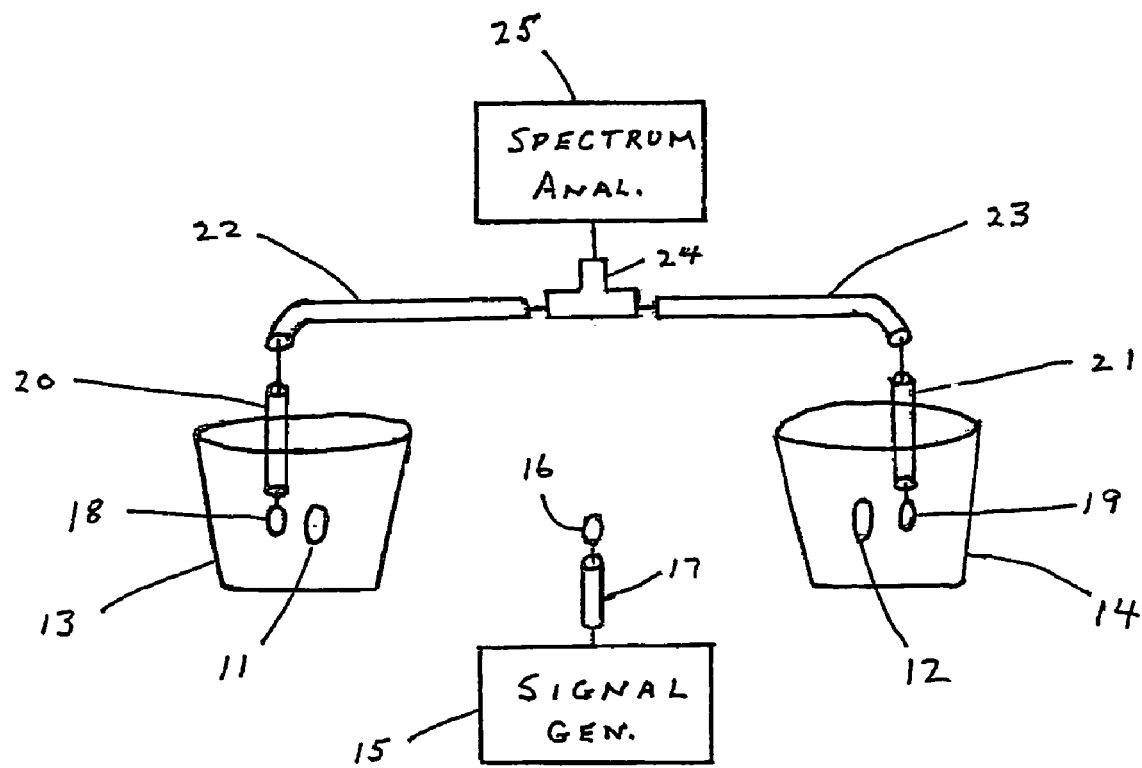
FIG. 2 is a schematic diagram of the experimental set-up used in the example.

A schematic diagram of the experimental set-up used to demonstrate the increase in S/N when two sensors are used, and the signals from the sensors are added coherently, is shown in FIG. 2. Two of the essentially identical coils are used as one sensor 11. Sensor 11 demonstrates the use of a sensor comprised of two coupled high temperature superconductor self-resonant planar coils. The other two essentially identical coils are used as the second sensor 12. The sensors 11 and 12 are each immersed in liquid nitrogen held in Nalgene® (Nalge Nunc International, Rochester, N.Y.) dewars 13 and 14, respectively, and each is tuned to 3.6 MHz. An Agilent E4433B Signal Generator (Agilent Technologies, Palo Alto, Calif.) 15 and a transmit loop 16 are used in place of a NQR source.

The transmit loop 16 is comprised of a loop of copper wire approximately 2 cm in diameter. The transmit loop 16 is placed so that the sensors 11 and 12 are approximately equidistant from it, i.e. about 0.5 m away from each of the sensors, with the plane of the transmit loop parallel to the planes of the coils of the sensors. The transmit loop is formed by removing the outer jacket and dielectric spacer from a piece of 0.080 inch (2 mm) coax cable 17. The transmit loop is formed by bending the inner conductor into a circle and soldering it to the outer jacket of the coax cable just outside the point where the jacket and dielectric are removed. The signal generator provided a −10 dBm signal at a frequency of 3.6 MHz. Two pick-up coils 18 and 19, each comprised of a loop of copper wire, are placed about 1 inch (2.5 cm) away from the sensors 11 and 12, respectively, with the planes of the pick-up coils parallel to the planes of the coils of the sensors. Each of the pick-up coils 18 and 19 is formed by removing the outer jacket and dielectric spacer from a piece of 0.080 inch (2 mm) coax cable 20 and 21, respectively. The loop is formed by bending the inner conductor into a circle and soldering it to the outer jacket of the coax cable just outside the point where the jacket and dielectric are removed. The coax cables 20 and 21 are each connected to a 93 ohm 2 m piece of RG62 cable 22 and 23, respectively, which are connected to a 50 ohm tee 24 combination point. This insured that the electrical phase along the two paths is essentially the same. The output of the tee 24 combination point is fed to a Spectrum Analyzer R&S FSP 25 (Rohde & Schwarz GmbbH & Co., KG, Munchen, Germany).

The signal with only one sensor present is compared to that obtained using the two sensors. The use of the two sensors resulted in a 6 dB increase in signal. This demonstrates the increase in S/N when two sensors are used to detect a frequency and the signals from the sensors are added coherently.

While the discussion herein is presented primarily in terms of the use of a coil as the transmit, receive or transmit and receive device, this invention is not limited thereto, and is applicable to transmit, receive and transmit and receive devices that may have a configuration other than that of a coil.

Where an apparatus or method of this invention is stated or described as comprising, including, containing, having, being composed of or being constituted by certain components or steps, it is to be understood, unless the statement or description explicitly provides to the contrary, that one or more components or steps other than those explicitly stated or described may be present in the apparatus or method. In an alternative embodiment, however, the apparatus or method of this invention may be stated or described as consisting essentially of certain components or steps, in which embodiment components or steps that would materially alter the principle of operation or the distinguishing characteristics of the apparatus or method would not be present therein. In a further alternative embodiment, the apparatus or method of this invention may be stated or described as consisting of certain components or steps, in which embodiment components or steps other than those as stated would not be present therein.

Where the indefinite article "a" or "an" is used with respect to a statement or description of the presence of a component in an apparatus, or a step in a method, of this invention, it is to be understood, unless the statement or description explicitly provides to the contrary, that the use of such indefinite article does not limit the presence of the component in the apparatus, or of the step in the method, to one in number.

What is claimed is:

1. A method of detecting nuclear quadrupole resonance in an object, comprising the steps of:
    a) providing two or more high temperature superconductor self-resonant planar coil sensors each tuned to a specified nuclear quadrupole resonance frequency, wherein each sensor is solely operative to detect the specified nuclear quadrupole resonance signal, each sensor being connected by an electrical path to a combination point;
    b) using a single shielded-loop resonator coil, to apply a radio frequency magnetic field to the object; and
    c) adjusting the signals detected by the sensors in accordance with the electrical path so that the signals are coherent with each other and add constructively at the combination point.

2. The method of claim 1, wherein the shielded-loop resonator coil is copper.

3. The method of claim 1, wherein each high temperature superconductor self-resonant planar coil is a $YBa_2Cu_3O_7$ or $Tl_2Ba_2CaCu_2O_8$ self-resonant planar coil.

4. The method of claim 1,
    wherein each sensor is essentially equidistant from the object, and
    wherein the electrical path from each sensor to the combination point is essentially identical so that the signals are coherent and add constructively at the combination point.

5. The method of claim 1, wherein each signal, before combination, is multiplied by a constant complex factor specific to the electrical path from each sensor to the combination point to correct for any phase differences between the signals so that the signals are coherent and add constructively at the combination point.

6. The method of claim 1, wherein the object comprises explosives, drugs or other contraband.

7. A nuclear quadrupole resonance detection system for detecting nuclear quadrupole resonance in an object, comprising:
    a) a single shielded-loop resonator coil for applying a radio frequency magnetic field to the object;
    b) two or more high temperature superconductor self-resonant planar coil sensors each tuned to a specified nuclear quadrupole resonance frequency, each sensor being operative solely to detect the specified nuclear quadrupole resonance signal, each sensor being connected by an electrical path to a combination point; and
    the nuclear quadrupole resonance signals detected by the sensors being adjusted in accordance with the electrical path connecting each sensor to the combination point so that the signals are coherent and add constructively at the combination point.

8. The detection system of claim 7, wherein each high temperature superconductor self-resonant planar coil is a $YBa_2Cu_3O_7$ or $Tl_2Ba_2CaCu_2O_8$ self-resonant planar coil.

9. The detection system of claim 7, wherein the shielded-loop resonator coil is copper.

10. The detection system of claim 7, wherein each signal, before combination, is multiplied by a constant complex factor specific to the electrical path from each sensor to the combination point to correct for any phase differences between the signals so that the signals are coherent and add constructively at the combination point.

11. The detection system of claim 7, wherein the object comprises explosives, drugs or other contraband.

12. The detection system of claim 7,
    wherein each sensor is essentially equidistant from the object, and
    wherein the electrical path from each sensor to the combination point is essentially identical so that the signals are coherent and add constructively at the combination point.

* * * * *